US00PP08947P

United States Patent [19]

Bradford et al.

[11] Patent Number: Plant 8,947

[45] Date of Patent: Oct. 18, 1994

[54] NECTARINE TREE (AUGUST SNOW)

[76] Inventors: Lowell G. Bradford, 12439 E. Savana Rd.; Norman G. Bradford, 11875 E. Savana Rd., both of Le Grand, Calif. 95333

[21] Appl. No.: 188,914

[22] Filed: Jan. 31, 1994

[51] Int. Cl.[5] ..... A01H 5/00

[52] U.S. Cl. ..... Plt./40.1

[58] Field of Search ..... Plt. 40.1, 41.1

*Primary Examiner*—James R. Feyrer

[57] ABSTRACT

The present invention relates to a nectarine tree and more particularly to a new and distinct variety broadly characterized by a large size, vigorous, productive and regular bearing tree. The fruit matures under the ecological conditions described approximately the first week in August, with first picking on Aug. 1, 1993. The fruit is uniformly large in size, nonacidic in flavor, globose to slightly oblong in shape, freestone in type, firm in texture, and nearly full red in skin color. The variety was a first generation cross using Bradcrim (U.S. Plant Pat. No. 8,461) white flesh nectarine as the seed parent and August Red (U.S. Plant Pat. No. 6,363) yellow flesh nectarine as the pollen parent.

1 Drawing Sheet

BACKGROUND OF THE VARIETY

In a continuing effort to improve the quality of fresh market and shipping fruits, we, the inventors, typically hybridize a large number of nectarine and peach seedlings each year. The present invention relates to a new and distinct variety of nectarine tree, which has been denominated varietally as "August Snow". The present variety was developed by us in 1987 as a first generation cross using Bradcrim (U.S. Plant Pat. No. 8,461) white flesh nectarine as the seed parent and August Red (U.S. Plant Pat. No. 6,363) yellow flesh nectarine as the pollen parent, in a cultivated area of our experimental orchard at Bradford Farms near Le Grand, Calif. in Merced County (San Joaquin Valley). Subsequent to origination of the present variety of nectarine tree, we asexually reproduced it by budding and grafting, and such reproduction of plant and fruit characteristics were true to the original plant in all respects.

The fruit produced by the present variety is most similar to its seed parent, the Bradcrim (U.S. Plant Pat. No. 8,461), by producing white flesh freestone nectarines that are nearly full red in skin color and non-acidic in flavor, but is distinguished therefrom and an improvement thereon by producing fruit that ripens thirty days later, that is larger in size, and that is much firmer in texture.

The present variety is similar to its selected pollen parent, August Red (U.S. Plant Pat. No. 6,363), by abundantly producing large sized, very firm, nectarines that are nearly full red in skin color, but is distinguished therefrom by producing fruit that is white flesh instead of yellow flesh, that is freestone instead of clingstone, and that is non-acidic in flavor instead of acidic.

DRAWING

The accompanying photograph exhibits four whole fruits positioned to display the characteristics of the skin color and form, one fruit divided along the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of eating ripe on Aug. 8, 1993. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Bark color.*—Light grayish brown [60. l.gy.Br].
- *Lenticels.*—Medium. Color: Dark orange yellow [72. d.OY]. Average size: $\frac{1}{4}$" [6.4 mm.].

Branches:
- *Size.*—Medium.
- *Texture.*—Medium.
- *Color.*—1st year wood topside: Light grayish red [18. l.gy.R]. 1st year wood underside: Brilliant yellow green [116. brill.YG]. Older Wood: Moderate brown [58. m.Br].
- *Lenticels.*—Medium, small.

Leaves:
- *Size.*—Large. Average length: 6" [152.4 mm.]. Average width: $1\frac{5}{8}$" [41.3 mm.].
- *Thickness.*—Medium.
- *Form.*—Elliptical.
- *Apex.*—Acuminate.
- *Base.*—Acute.
- *Surface.*—Smooth.
- *Color.*—Dorsal surface: Deep yellow green [118. deep YG]. Ventral surface: Moderate yellow green [120. m.YG].
- *Margin.*—Finely serrate.
- *Venation.*—Pennately net veined. Color: Light yellow green [119. l.YG] with some moderate red [15. m.R] tinting.

*Petiole.*—Average length: ⅜" [9.5 mm.]. Average thickness: 1/16" [1.6 mm.]. Color: Light yellow green [119. l.YG].

*Stipules.*—Moderate. Average length: ¼" [6.4 mm.].

*Glands.*—Numbers: Mostly 2 per leaf. Position: Both oppositely and alternately positioned on petiole and base of blade. Size: Small. Form: Globose. Color: Light yellow green [119. l.YG].

Flower Buds:

*Hardiness.*—Hardy.

*Size.*—Medium.

*Length.*—Medium.

*Form.*—Free.

*Surface.*—Pubescent.

Flowers:

*Blooming period.*—Medium as compared with other varieties.

*Size.*—Large.

*Color.*—Moderate pink [5. m.Pk].

FRUIT

Maturity when described: Firm ripe, Aug. 8, 1993.

Date of first picking: Aug. 1. 1993.

Date of last picking: Aug. 10, 1993.

Size: Uniform, large.

*Average diameter axially.*—2⅝" [66.7 mm.].

*Average traversely in suture plane.*—2½" [63.5 mm.].

Form: Globose to slightly oblong, slightly variable, slightly unsymmetrical.

*Longitudinal section form.*—Round to slightly heart shaped.

*Transverse section through diameter.*—Round.

Suture: An inconspicuous shallow line extending from the base and discontinuing at the apex, sharp near the base.

Ventral surface: Rounded, slightly lipped toward the apex.

Lips: Slightly unequal.

Cavity: Flaring, slightly elongated in suture plane, suture showing on one side.

*Depth.*—⅜" [9.5 mm.].

*Breadth.*—¾" [19.1 mm.].

Base: Slightly cuneate, slightly truncate.

Apex: Short, slightly protruding, few mammiform.

Pistil point: Somewhat oblique.

Stem: Medium.

*Average length.*—5/16" to ⅜" [7.9–9.5 mm.].

*Average width.*—3/16" [4.8 mm.].

Skin:

*Thickness.*—Medium.

Texture.—Medium.

*Tenacity.*—Tenacious to flesh.

*Tendency to crack.*—Slight.

*Color.*—Dark red [16. d.R] in sunlight over a yellowish white [92. yWhite] background.

Flesh:

*Color.*—White [263. White] with no bleeding at skin, slight moderate red [15. m.R] streaking near stone.

*Surface of pit cavity.*—Moderate red [15. m.R] fibers.

*Amygdalin.*—Scarce.

*Juice.*—Abundant, rich.

*Texture.*—Firm. somewhat rubbery after cold storage, fine, crisp.

*Fibers.*—Abundant, fine, tender.

*Ripens.*—Evenly.

*Flavor.*—Subacidic to nonacidic and sweet.

*Aroma.*—Slight.

*Eating quality.*—Very good.

STONE

Type: Freestone.

Form: Elliptical.

Base: Oblique.

Apex: Acuminate.

Sides: Equal.

Surface: Irregularly furrowed toward the apex and pitted toward the base.

Ridges: Jagged toward the base.

Color: Strong brown [55. s.Br] to moderate brown [58. m.Br].

Pit wall: 3/16" [4.8 mm.] thick.

Tendency to split: Slight.

Kernel:

*Form.*—oval.

*Taste.*—Bitter.

*Viable.*—Yes.

*Average width.*—7/16" to ½" [11.1–12.7 mm.].

*Average length.*—11/16" to ¾" [17.5–19.1 mm.].

*Skin color.*—Deep orange yellow [69. deep OY].

*Pellicle color.*—Grayish yellowish brown [80. gy-.yBr].

*Amygdalin.*—Abundant.

USE

Market: Fresh and long distance shipping.

Keeping quality: Very good.

Shipping quality: Good.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to its seed parent, the Bradcrim (U.S. Plant Pat. No. 8,461), by producing white flesh freestone nectarines that are nearly full red in skin color and non-acidic in flavor, but is distinguished therefrom and an improvement thereon by producing fruit that ripens thirty days later, that is larger in size, and that is much firmer in texture.

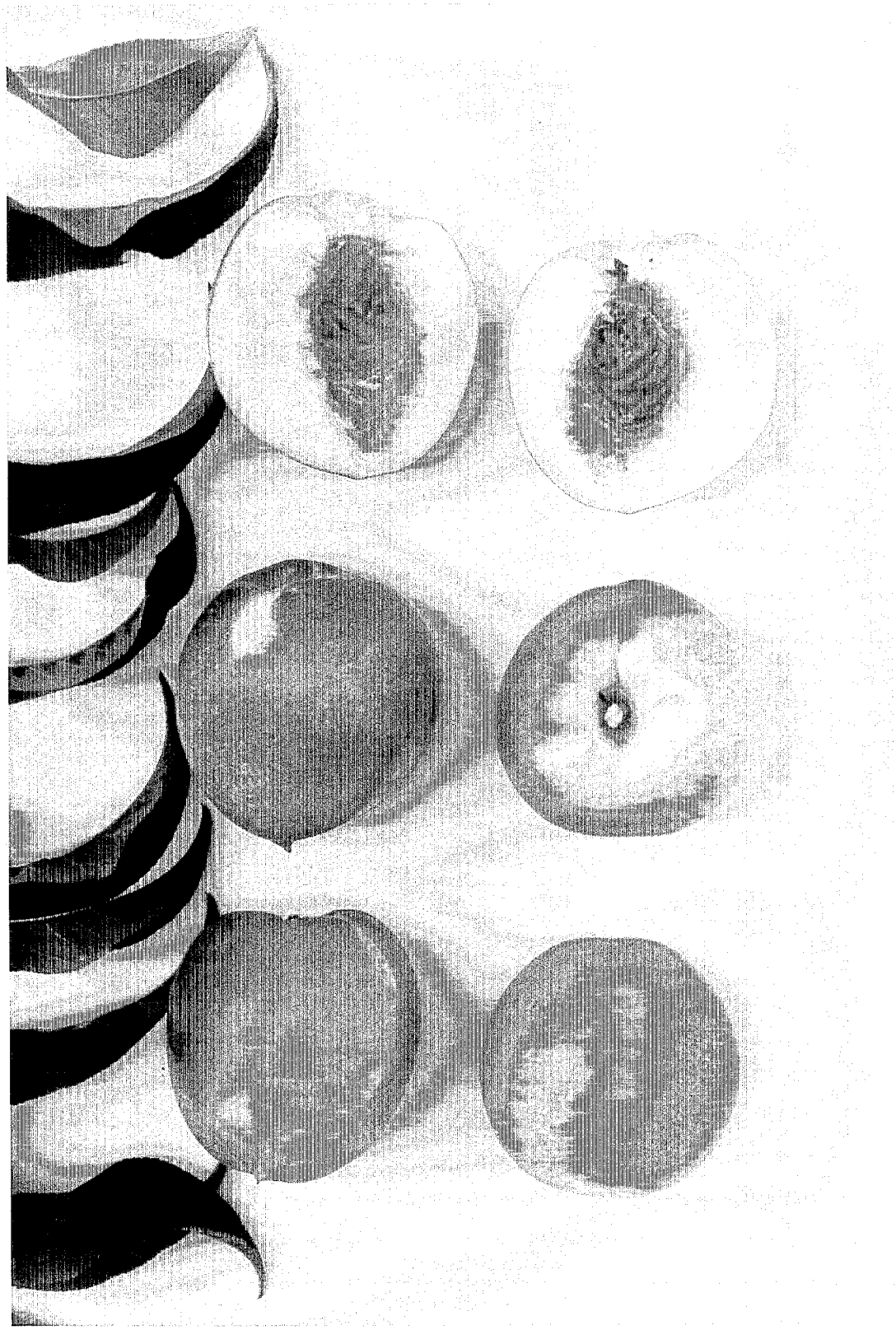

* * * * *